United States Patent
Nagasawa (10) Patent No.: US 7,781,703 B2
(45) Date of Patent: Aug. 24, 2010

(54) THERMAL ANALYZER

(75) Inventor: Jun Nagasawa, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 399 days.

(21) Appl. No.: 11/809,623

(22) Filed: Jun. 1, 2007

(65) Prior Publication Data
US 2008/0000402 A1    Jan. 3, 2008

(30) Foreign Application Priority Data
Jun. 5, 2006    (JP) .............................. 2006-155996

(51) Int. Cl.
*B23K 13/08* (2006.01)
*G01N 25/00* (2006.01)
(52) U.S. Cl. ........................................ 219/482; 374/11
(58) Field of Classification Search ................ 219/482; 110/185; 702/99, 130; 374/10–13
See application file for complete search history.

(56) References Cited
U.S. PATENT DOCUMENTS

| | | | | |
|---|---|---|---|---|
| 4,246,641 A | * | 1/1981 | Babil et al. | ................... 702/99 |
| 5,875,416 A | * | 2/1999 | Kanno | ........................ 702/130 |
| 6,210,035 B1 | * | 4/2001 | Nakamura | ..................... 374/11 |
| 2002/0085615 A1 | * | 7/2002 | Nakamura et al. | ............ 374/12 |
| 2004/0059507 A1 | * | 3/2004 | Nagasawa | ...................... 702/2 |

FOREIGN PATENT DOCUMENTS

| | | |
|---|---|---|
| JP | H01-174954 | 7/1989 |
| JP | 09101275 A  * | 4/1997 |

\* cited by examiner

*Primary Examiner*—Tu B Hoang
*Assistant Examiner*—Hung Nguyen
(74) *Attorney, Agent, or Firm*—Brinks Hofer Gilson & Lione (57) ABSTRACT

The thermal analyzer comprises temperature deviation approximation formula holder which holds an approximate formula of a temperature deviation between sample and furnace and an elevating or lowering rate of the temperature of furnace during measuring the temperature deviation, programmed temperature corrector which corrects a programmed temperature in proportion to the elevating or lowering rate of the temperature. So that, since the temperature deviation is corrected in proportion to the elevating or lowering rate of the temperature program, the temperature deviation between sample and furnace is controlled to diminish when heating or cooling the sample using the temperature program which elevates or lowers the temperature of the sample or the furnace.

2 Claims, 6 Drawing Sheets

21 SAMPLE
22 PROPERTY SENSOR
23 HEATING FURNACE
24 MEASURING UNIT
25 PROGRAMMED TEMPERATURE GENERATOR
26 TEMPERATURE DEVIATION APPROXIMATION FORMULA HOLDER
27 TEMPERATURE DEVIATION APPROXIMATION FORMULA RETRIEVAL UNIT
28 PROGRAMMED TEMPERATURE CORRECTOR
29 FEEDBACK CONTROL CIRCUIT
30 HEATING FURNACE CONTROLLER

FIG. 1

1 SAMPLE
2 PROPERTY SENSOR
3 HEATING FURNACE
4 MEASURING UNIT
5 PROGRAMMED TEMPERATURE GENERATOR
6 TEMPERATURE DEVIATION APPROXIMATION FORMULA HOLDER
8 PROGRAMMED TEMPERATURE CORRECTOR
9 FEEDBACK CONTROL CIRCUIT
10 HEATING FURNACE CONTROLLER

FIG. 2

21 SAMPLE
22 PROPERTY SENSOR
23 HEATING FURNACE
24 MEASURING UNIT
25 PROGRAMMED TEMPERATURE GENERATOR
26 TEMPERATURE DEVIATION APPROXIMATION FORMULA HOLDER
27 TEMPERATURE DEVIATION APPROXIMATION FORMULA RETRIEVAL UNIT
28 PROGRAMMED TEMPERATURE CORRECTOR
29 FEEDBACK CONTROL CIRCUIT
30 HEATING FURNACE CONTROLLER

THERMAL ANALYZER

This application claims priority under 35 U.S.C. §119 to Japanese Patent Application No. JP2006-155996 filed Jun. 5, 2006, the entire content of which is hereby incorporated by reference.

BACKGROUND OF THE INVENTION

The present invention relates to a thermal analyzer for measuring the dependency of properties of a material upon the temperature. More specifically, the invention relates to a thermal analyzer for measuring the dependency of properties of a material upon the temperature by controlling the temperature according to a temperature program which elevates or lowers the temperature of a heating furnace for heating the sample at a constant rate.

In a conventional heat analyzer as disclosed in, for example, JP-A-1-174954, the heating furnace is maintained at a constant temperature prior to making the measurement to examine the relationship between the sample/heating furnace temperature deviation and the sample temperature. When really making the measurement, the temperature deviation is added to the programmed temperature, and thus the temperature of the heating furnace is controlled to be somewhat higher than its programmed temperature, so that the sample temperature is controlled to approach its programmed temperature.

In a feedback loop for controlling the temperature of the heating furnace, further, the temperature is controlled so as to bring the sample temperature close to its programmed temperature by using the sample temperature as the feedback quantity instead of using the heating furnace temperature.

In the heat analyzer, the heating furnace is controlled by feedback such as PID control so that the temperature of the heating furnace is brought into agreement with the programmed temperature. Therefore, the temperature of the heating furnace is so controlled as to follow the programmed temperature at all times. Between the heating furnace and the sample, however, there is loss due to heat resistance and time lag and, therefore, there is a temperature deviation at all times between the heating furnace and the sample. This will be no problem if the temperature deviation is constant. In practice, however, the temperature deviation varies depending upon the temperature of the heating furnace and the rate of elevating or lowering the temperature. In general, the deviation increases with increase in the temperature of the heating furnace and with an increase in the rate of elevating or lowering the temperature.

Figure 3:
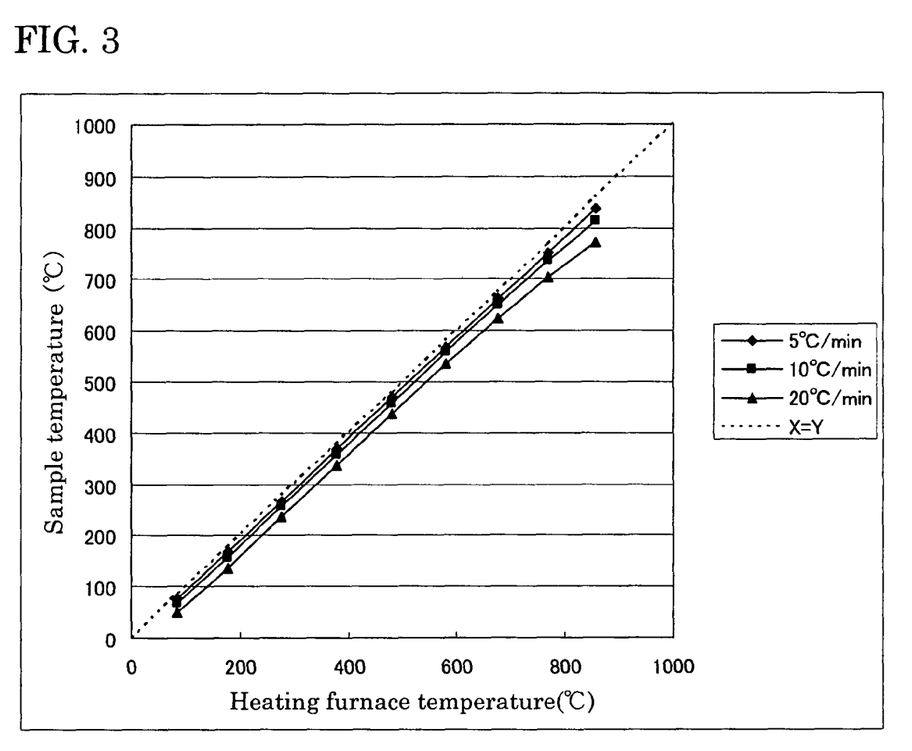
FIG. 3 is a graph of sample temperatures plotted against the temperature of the heating furnace at the time of elevating the temperature.
Figure 4:
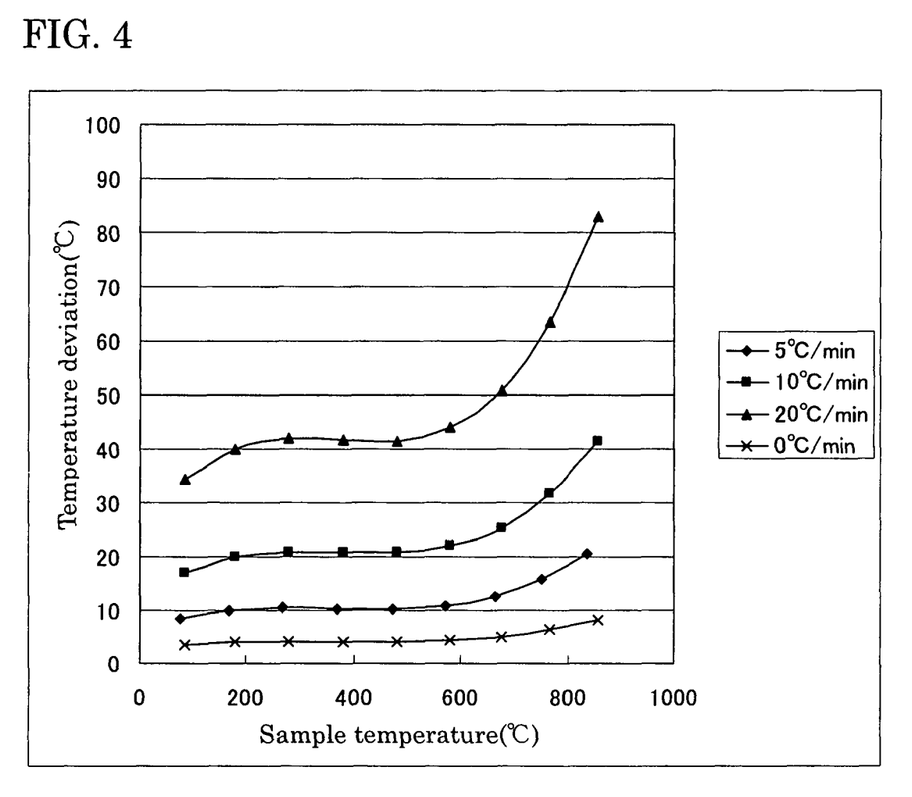
FIG. 4 is a graph showing temperature deviations between the sample and the heating furnace plotted against the sample temperature at the time of elevating the temperature.
Figure 5:
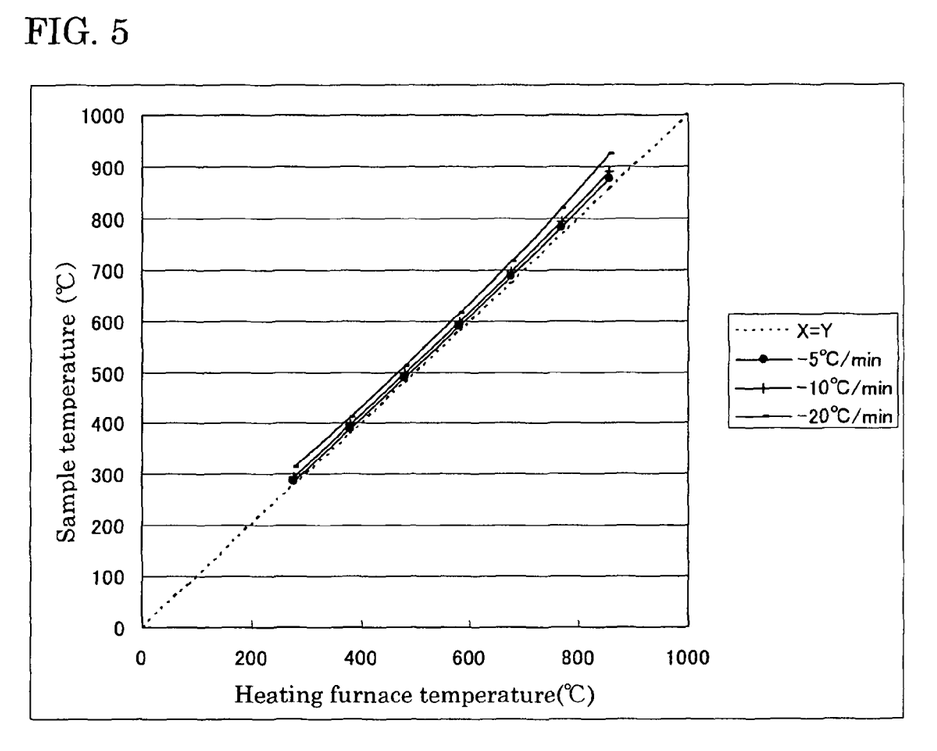
FIG. 5 is a graph showing sample temperatures plotted against the temperature of the heating furnace at the time of lowering the temperature.

FIGS. 3 and 5 illustrate examples of measuring a relationship between the temperature of the heating furnace and the sample temperature. FIG. 3 illustrates a case of when the temperature is elevated and FIG. 5 illustrates a case of when the temperature is lowered. The temperature deviation between the heating furnace and the sample increases with an increase in the temperature zone or with an increase in the rate of elevating the temperature (lowering the temperature). The same data are also used in FIGS. 4 and 6 where the X-axis represents the sample temperature and the Y-axis represents the deviation of temperature between the heating furnace and the sample. The temperature deviation increases nearly in proportion to the rate of elevating the temperature (lowering the temperature). FIG. 4 includes additional approximation curves of temperature deviations held constant at each of the temperatures, as a curve of 0° C./min. When held constant (rate of temperature elevation is 0) as described above, the temperature deviation becomes still smaller.

In the former case according to the above prior art, the temperature deviations are examined in a state where the temperatures are maintained constant, and the relationship between the temperature of the heating surface and the sample temperature is polynomially approximated so that Temperature of the heating furnace=$f$(sample temperature)

and the correction is effected by using the approximation formula $f$ at the time of making a measurement. In the case of the temperature program maintaining a constant temperature, the heating furnace and the sample temperature are maintained to be in good agreement as desired.

However, the temperature program which elevates or lowers the temperature at a constant rate has the problem of increased temperature deviation between the heating furnace and the sample. In particular, the temperature deviation increases with an increase in the rate of elevating the temperature or in the rate of lowering the temperature.

Further, the latter case has the problem that it is difficult to execute stable control due to the time lag in the change of the feedback value (sample temperature) which indicates the temperature of the heating furnace which is the object to be controlled.

It is the problem of the present invention to provide a thermal analyzer which enables the temperature of a sample to accurately follow the programmed temperature even in a temperature program which elevates or lowers the temperature at a constant rate.

SUMMARY OF THE INVENTION

In order to solve the above problem, the invention provides a thermal analyzer for measuring the dependency of properties of a material upon the temperature by controlling the temperature according to a temperature program which elevates or lowers the temperature of a heating furnace for heating the sample at a constant rate, wherein deviation in the temperature between the sample and the heating furnace is corrected in proportion to the rate of elevating the temperature or to the rate of lowering the temperature set in the temperature program.

That is, to solve the above problem, the invention provides a thermal analyzer comprising a heating furnace for heating a sample, which is provided with a property sensor; a measuring unit for inputting property signals output from the property sensor of the heating furnace and for outputting these signals as measurement signals; a programmed temperature generator for outputting a programmed temperature as a function of time; a temperature deviation approximation formula holder holding an approximation formula for the temperature deviation between the heating furnace and the sample whose temperature is elevating or lowering at a predetermined rate, and storing the rate of elevating or lowering the temperature; a programmed temperature corrector for correcting the programmed temperature and for outputting it as a corrected programmed temperature; a feedback control circuit for outputting a heating furnace-heating electric power value with the temperature of the heating furnace as the feedback amount, so that the temperature of the heating furnace is brought into agreement with the corrected programmed temperature; and a heating furnace controller for feeding the heating furnace-heating electric power to the heating furnace.

According to the invention, a temperature deviation between the sample and the heating furnace is corrected in proportion to the rate of elevating or lowering the temperature of a temperature program. Therefore, the temperature deviation is corrected in an optimum manner at all times depending upon the rate of elevating or lowering the temperature set in the temperature program, and the temperature of the sample can be accurately varied according to the temperature program.

In the feedback loop for controlling the temperature of the heating furnace, further, the temperature of the heating furnace which is the object to be controlled is directly used as the feedback quantity. Therefore, the temperature can be controlled maintaining stability at all times with small time lag in the feedback loop.

DETAILED DESCRIPTION OF THE PREFERRED EMBODIMENT

The best mode for carrying out the invention will now be described as Examples 1 and 2 with reference to the drawings.

EXAMPLE 1

Figure 1:
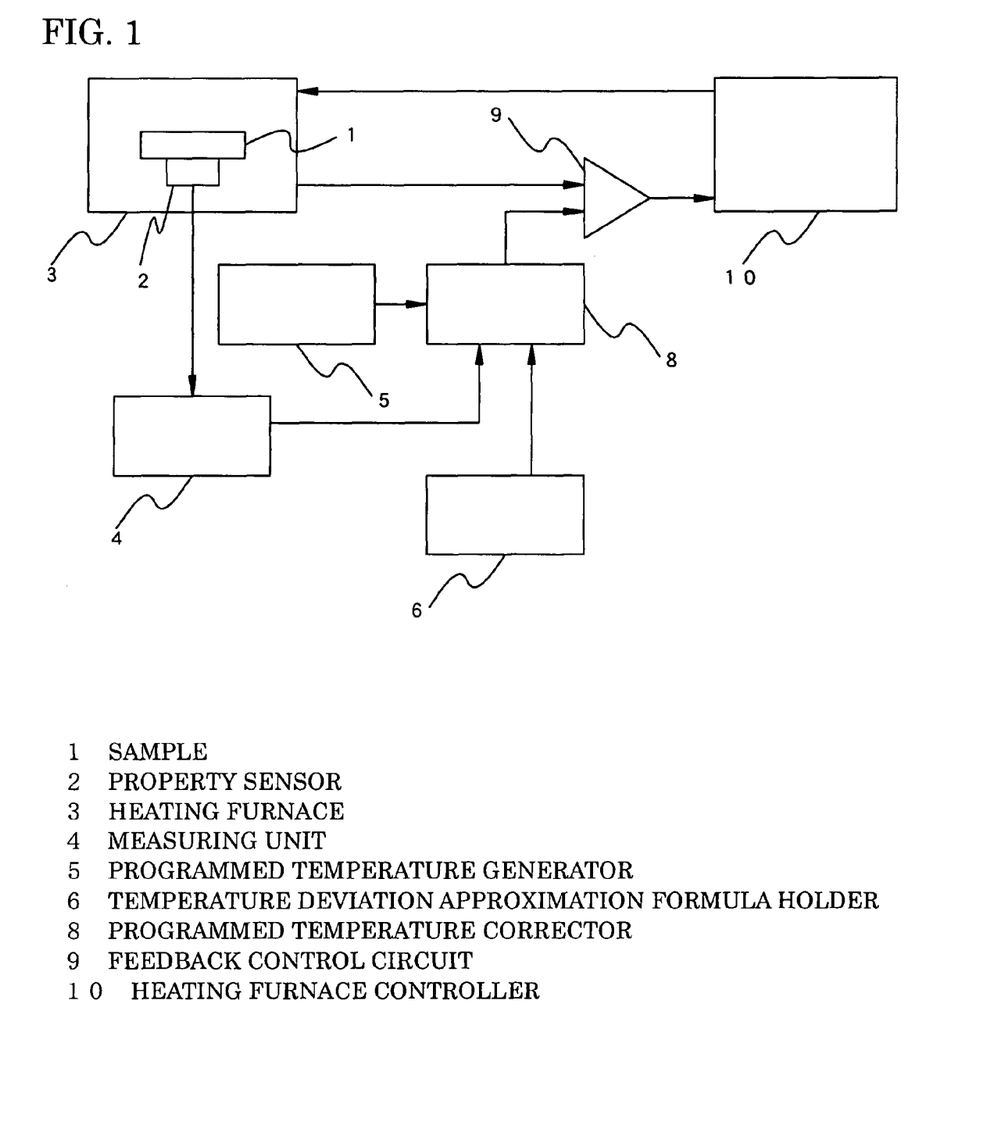
FIG. 1 illustrates a heat analyzer according to Example 1 of the invention.

FIG. 1 illustrates a heat analyzer according to Example 1 of the present invention, wherein reference numeral 1 is a sample to be measured which is placed in a heating furnace 3 equipped with a property sensor 2. A measuring unit 4 is connected to the heating furnace 3, inputs property signals output from the property sensor 2, performs calculation upon them, and outputs them as measurement signals to a data processor such as PC (not shown). In the case of a DSC device, the measurement signals are sample temperature, differential heat, etc. In the case of a TG/DTA device, the measurement signals are sample temperature, weight, and differential heat. A programmed temperature generator 5 holds a temperature program for heating the sample 1, and outputs programmed temperatures as a function of time.

Here, if a relationship between the sample 1/heating furnace temperature 3 temperature deviation and the sample temperature is a function f as expressed by the formula, then the temperature deviation from the sample temperature can be measured while heating or cooling the heating furnace, and the function f can be given polynomial approximation.

Temperature deviation=$f$(sample temperature)  (1)

Hereinafter, the function f found by the polynomial approximation as described above is called temperature deviation approximation formula f.

A temperature deviation approximation formula holder 6 holds the temperature deviation approximation formula f and the rate of elevating or lowering the temperature at the time of measuring the temperature deviation. A programmed temperature corrector 8 is connected to the measuring unit 4, to the programmed temperature generator 5, to the temperature deviation approximation formula holder 6 and to a feedback control circuit 9, inputs the sample temperature from the measuring unit 4, a programmed temperature from the programmed temperature generator 5, and a temperature deviation approximation formula and the rate of elevating or lowering the temperature at the time of measuring the temperature deviation from the temperature deviation approximation formula holder 6, corrects the programmed temperature and outputs the result as a corrected programmed temperature to the feedback control circuit 9.

The feedback control circuit 9 is connected to the heating furnace 3, to the programmed temperature corrector 8 and to a heating furnace controller 10, executes a well-known PID calculation of the operation needed so that the temperature of the heating furnace input from the heating furnace 3 is brought into agreement with the corrected programmed temperature input from the programmed temperature corrector 8, and outputs the result as a heating furnace-heating electric power value to the heating furnace controller 10. The heating furnace controller 10 feeds heating furnace-heating electric power to the heating furnace 3 according to the heating furnace-heating electric power value input from the feedback control circuit 9. The feedback control circuit 9, heating furnace controller 10 and heating furnace 3 constitute a feedback loop for bringing the temperature of the heating furnace into agreement with the corrected programmed temperature.

Prior to making a measurement, the difference between the sample 1/heating furnace 3 temperature deviations and the sample temperature are measured while heating or cooling the heating furnace 3 at a constant rate, and these difference values are polynomially approximated to find a temperature deviation approximation formula f. The temperature deviation approximation formula f, and the rate of elevating or lowering the temperature at the time of measuring temperature deviations, are set in the temperature deviation approximation formula holder 6.

Next, a desired temperature program is set in the programmed temperature generator 5 to start measurement. As the measurement starts, the programmed temperature generator 5 outputs a programmed temperature as a function of time to the programmed temperature corrector 8. The programmed temperature corrector 8 inputs the sample temperature from the measuring unit 4, inputs the temperature deviation approximation formula f and the rate of elevating the temperature (lowering the temperature) from the temperature deviation approximation formula holder 6, corrects the programmed temperature based thereupon, and outputs the corrected programmed temperature to the feedback control circuit 9. The feedback loop constituted by the feedback control circuit 9, heating furnace controller 10, and heating furnace 3, executes a feedback control so that the temperature of the heating furnace 3 is brought into agreement with the corrected programmed temperature.

Operation of the programmed temperature corrector 8 will now be described in detail. The programmed temperature corrector 8, first, enters the sample temperature Ts in the temperature deviation approximation formula f to calculate a sample 1/heating furnace 3 temperature deviation approximation value $\Delta T$ at the present sample temperature Ts (following formula), $\Delta T = f(Ts)$  (2)

The temperature deviation approximate value ΔT is a temperature deviation approximation value based on the rate of elevating or lowering the temperature at the time of measuring the temperature deviation.

Described below is a case where the temperature deviations are measured while elevating the temperature, and a temperature program for elevating the temperature is used. Since the temperature deviation varies in proportion to the rate of elevating the temperature, the temperature deviation approximation value Δ is multiplied by a ratio of the present rate of elevating the temperature and the rate of elevating the temperature at the time of measuring the temperature deviation in order to find a corrected temperature deviation approximation value ΔT'. The present rate of elevating the temperature used here is the programmed rate of elevating the temperature, namely, a time differentiation of the programmed temperature.

The ratio "a" of the programmed rate of elevating the temperature and the rate of elevating the temperature at the time of measuring the temperature deviation is expressed by the following formula:

a=programmed rate of elevating the temperature/rate of elevating the temperature at the time of measuring the temperature deviation The corrected temperature deviation approximate value ΔT' is as expressed by the following formula.

$$\Delta T' = a \times \Delta T \quad (3)$$

The corrected temperature deviation approximate value ΔT' is added to the programmed temperature which is, then, output as corrected programmed temperature (following formula).

Corrected programmed temperature=programmed temperature+$\Delta T'$

In the foregoing was described the case where the temperature deviation was measured while elevating the temperature, and a temperature program of while elevating the temperature was used. In the case of the temperature program while lowering the temperature, too, the programmed rate of elevating the temperature assumes a minus value and the corrected temperature deviation approximate value ΔT' becomes a minus temperature in the formula (3) and, therefore, the temperature is properly corrected.

Figure 6:
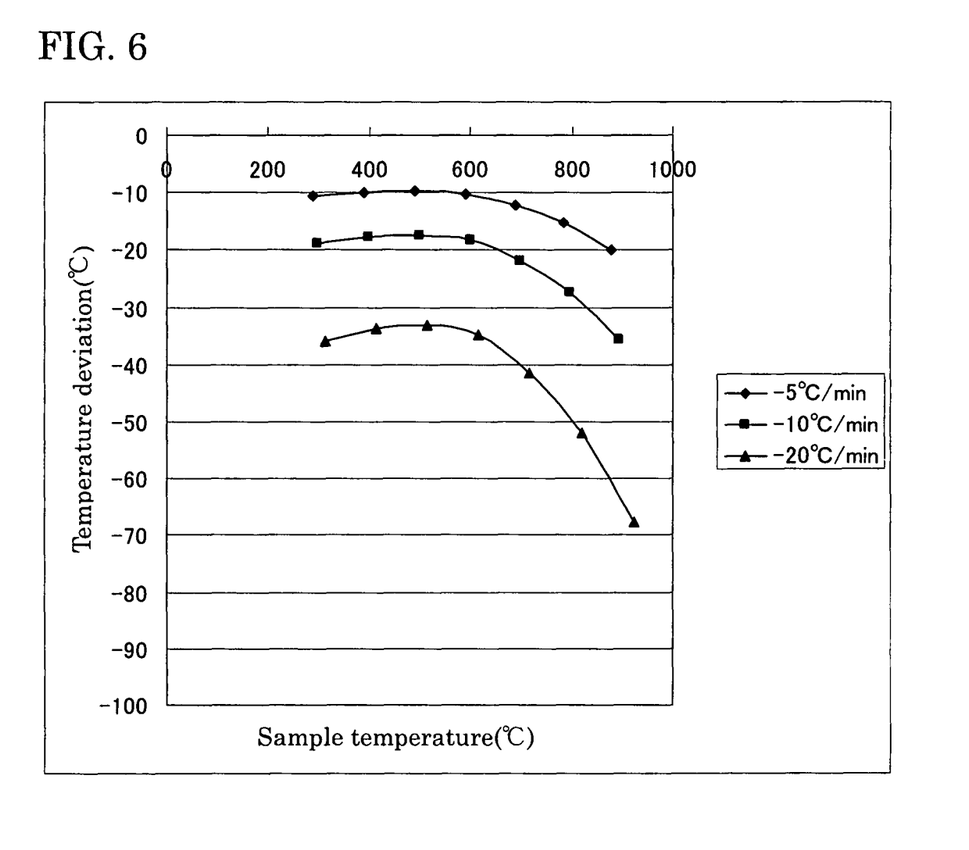
FIG. 6 is a graph showing temperature deviations between the sample and the heating furnace plotted against the sample temperature at the time of lowering the temperature.

As will be learned from FIGS. 4 and 6, at the time of elevating the temperature and lowering the temperature, the temperature deviation curve has nearly the same shape but has the opposite signs. Therefore, the temperature program can be properly corrected at the time of lowering the temperature, too, by using the temperature deviation approximation value found at the time of elevating the temperature. Namely, the same holds in the opposite case, too. Therefore, the temperature deviation approximation formula may be determined either when the temperature is being elevated or when the temperature is being lowered, and the temperature programs both when the temperature is being elevated and when the temperature is being lowered can be based on one temperature deviation approximation formula.

As described above, the temperature deviation is corrected in proportion to the rate of elevating or lowering the temperature set in the temperature program. It is, therefore, made possible to further decrease the temperature deviation between the sample and the heating furnace using various temperature programs for various rates of elevating or lowering the temperature to accomplish the object.

EXAMPLE 2

Figure 2:
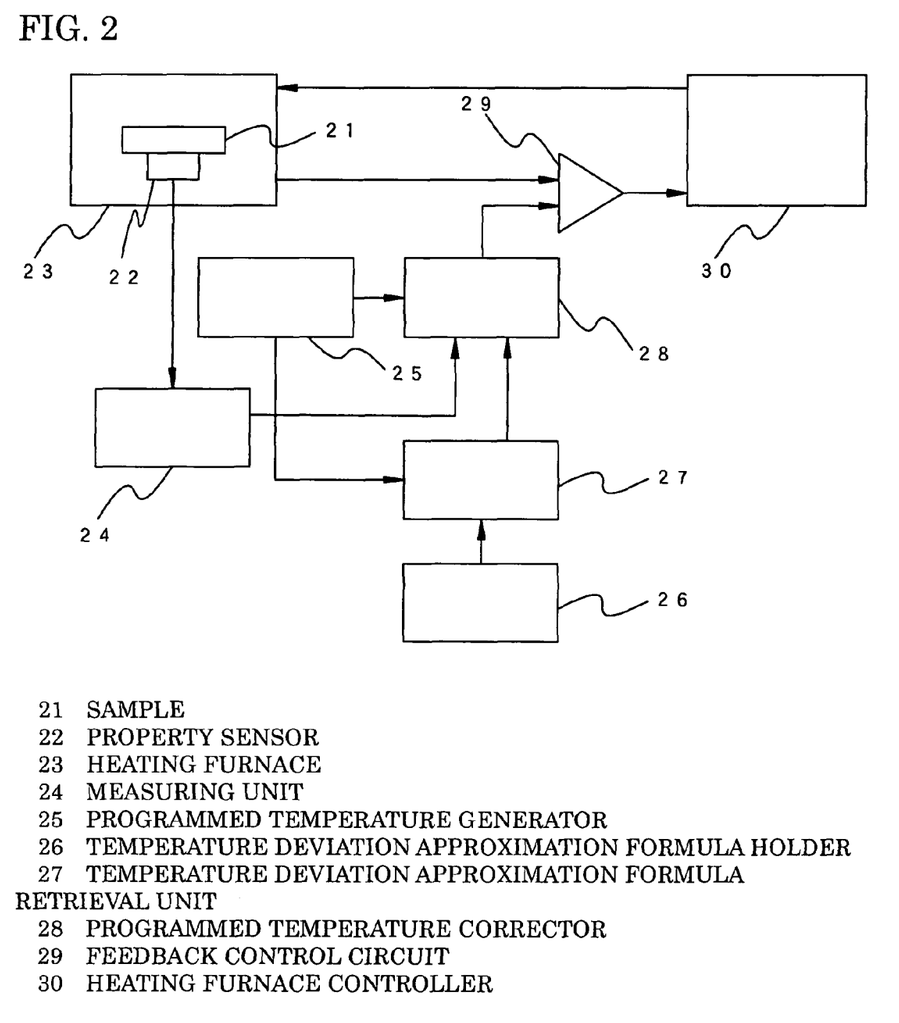
FIG. 2 illustrates a heat analyzer according to Example 2 of the invention.

FIG. 2 illustrates a heat analyzer according to Example 2 of the present invention, wherein a sample 21, a property sensor 22, a heating furnace 23, a measuring unit 24, a programmed temperature generator 25, a feedback control circuit 29 and a heating furnace controller 30 are the same as the sample 1, the property sensor 2, the heating furnace 3, the measuring unit 4, the program temperature generator 5, the feedback control circuit 9 and the heating furnace controller 10 in Example 1.

The difference from Example 1 is that the temperature deviation approximation formula holder 26 holds a plurality of sets of a temperature deviation approximation formula and a rate of elevating or lowering the temperature, is connected to the programmed temperature generator 25, to the temperature deviation approximation formula holder 26 and to the programmed temperature corrector 28, and includes a temperature deviation approximation formula retrieval unit 27 which retrieves a temperature deviation approximation formula from the temperature deviation approximation formula holder 26 by using, as a key, the programmed rate of elevating the temperature or lowering the temperature, and outputs the temperature deviation approximation formula to the programmed temperature corrector 28, wherein the programmed temperature corrector 28 corrects the programmed temperature based on the temperature deviation approximation formula output from the temperature deviation approximation formula retrieval unit 27 and outputs it as a corrected programmed temperature.

In calculating the temperature deviation approximation formula prior to making a measurement in Example 2, temperature deviations are measured in the cases of a plurality of rates of elevating or lowering the temperature, and a plurality of temperature deviation approximation formulas are calculated. It is desired to measure the temperature deviations at rates of elevating or lowering the temperature that are scheduled to be used at the time of making a measurement. A temperature deviation approximation formula and its corresponding rate of elevating or lowering the temperature at the time of measuring the temperature deviation are regarded to constitute a set. A plurality of sets can be obtained and are set in the temperature deviation approximation formula holder 26. When the temperature programs that maintain constant temperatures are to be used at the time of making a measurement, temperature deviation approximation formulas are found maintaining each of the temperatures constant (curve of 0° C./min in FIG. 4) and are set in the temperature deviation approximation formula holder 26 as temperature deviation approximation formulas for a zero rate of elevating the temperature. This makes it possible to effect an optimum correction also in the case of using a temperature program maintained at a constant temperature.

As the measurement starts, the programmed temperature generator 25 outputs programmed temperatures as a function of time. The temperature deviation approximation formula retrieval unit 27 inputs the programmed temperatures from the programmed temperature generator 25, and retrieves the temperature elevating or lowering rate held by the temperature deviation approximation formula holder 26 that is in agreement with the programmed rate of elevating the temperature which is a time differentiation of the programmed temperatures at the time of measuring the temperature deviation. When there is found the one that is in agreement, the temperature deviation approximation formula retrieval unit 27 obtains, from the temperature deviation approximation formula holder 26, the temperature deviation approximation formula f that constitutes a set with the rate of elevating or lowering the temperature at the time of measuring the temperature deviation, and outputs it to the programmed temperature corrector 28.

When there is found no rate of elevating or lowering the temperature that is in complete agreement, the temperature deviation approximation formula retrieval unit 27 outputs a temperature deviation approximation formula by using either one of the methods described below.

A first method comprises retrieving, from the temperature deviation approximation formula holder 26, the rate of elevating or lowering the temperature at the time of measuring the temperature deviation which is closest to the programmed rate of elevating the temperature or lowering the temperature, retrieving, from the temperature deviation approximation formula holder 26, the temperature deviation approximation formula f that constitutes a set with the retrieved rate of elevating or lowering the temperature, and outputting this set as the temperature deviation approximation formula f to the programmed temperature corrector 28.

A second method comprises finding the temperature deviation approximation formula f by the above first method, multiplying the temperature deviation approximation formula f by the ratio a between the programmed rate of elevating the temperature and the rate of elevating the temperature at the time of measuring the temperature deviation as in the following formula to form a new temperature deviation approximation formula fnew.

a=programmed rate of elevating the temperature/rate of elevating the temperature at the time of measuring the temperature deviation $$f_{new} = a \times f$$

The $f_{new}$ is output as the temperature deviation approximation formula f.

The programmed temperature corrector 28 inputs the temperature deviation approximation formula f from the temperature deviation approximation formula retrieval unit 27, inputs the sample temperature Ts from the measuring unit 24, and calculates the temperature deviation approximation value ΔT according to the following formula.

$$\Delta T = f(Ts)$$

The temperature deviation ΔT is added to the programmed temperature as in the following formula, and a corrected programmed temperature is output.

Corrected programmed temperature=programmed temperature+ΔT

A feedback loop constituted by the feedback control circuit 29, heating furnace controller 30 and heating furnace 23, executes a feedback control in a manner that the temperature of the heating furnace 23 is brought into agreement with the corrected programmed temperature.

Upon measuring the temperature deviation between the sample and the heating furnace in advance based on the rate of elevating or lowering the temperature at the time of making a measurement, the temperature deviation can be corrected in an optimum manner according to the rate of elevating or lowering the temperature at the time of making the measurement. Further, even if the rates of elevating or lowering the temperature when the temperature deviation was measured and when heating furnace temperature is measured are different, the temperature deviation can be corrected by using a better approximation value of temperature deviation based on temperature elevation rate, and so the temperature of the sample can be accurately controlled.

In the above Examples, the heating furnace and the sample are spaced apart from each other and, besides, a separator wall for purging gas is provided, creating a large temperature difference between the heating furnace and the sample. In the case of this constitution, the principle is easy to comprehend and a distinguished effect is exhibited. Not being limited thereto only, a similar effect is obtained even with the general heat analyzers.

In these Examples, the PID operation was carried out by utilizing the feedback control circuits 9 and 29. However, the invention can be placed in practice even by using any other method of executing the feedback control not being limited to the PID operation only, as a matter of course.

The measuring units 4 and 24, programmed temperature generators 5 and 25, temperature deviation approximation formula holders 6 and 26, temperature deviation approximation formula retrieval unit 27, programmed temperature correctors 8 and 28, and feedback control circuits 9 and 29 can be constituted by using either hardware or software, and its selection does not impose any limitation on the content of the invention, as a matter of course.

What is claimed is:

1. A thermal analyzer comprising:
    a heating furnace that changes a temperature of a sample and comprises a property sensor for measuring properties of the sample;
    a measuring unit that receives property signals output from the property sensor and that outputs the property signals as measurement signals;
    a programmed temperature generator that outputs a programmed temperature of the heating furnace as a function of time;
    a programmed temperature corrector connected to the measuring unit and to the programmed temperature generator, wherein the programmed temperature corrector corrects the programmed temperature of the heating furnace and outputs a corrected programmed temperature;
    a feedback control circuit connected to the heating furnace and to the programmed temperature corrector, wherein the feedback control circuit receives the temperature of the heating furnace as a feedback quantity and outputs an electric power value of a heater of the heating furnace so that the temperature of the heating furnace is brought into agreement with the corrected programmed temperature;
    a heating furnace controller connected to the heating furnace and to the feedback control circuit, wherein the heating furnace controller supplies to the heating furnace an electric power value equal to the electric power value outputted from the feedback control circuit; and
    a temperature deviation approximation formula holder connected to the programmed temperature corrector, wherein the temperature deviation approximation formula holder stores a set comprising a first rate of elevating or lowering temperature of the heating furnace and a temperature deviation approximation formula,
    wherein the temperature deviation approximation formula functionally approximates a temperature deviation between the heating furnace and the sample at the first rate of elevating or lowering temperature;
    wherein the programmed temperature corrector corrects the programmed temperature of the heating furnace based on the temperature deviation approximation formula, the first rate of elevating or lowering temperature, the temperature of the sample, and a second rate of elevating or lowering temperature of the programmed temperature, and outputs the corrected programmed temperature;

wherein the second rate of elevating or lowering temperature of the programmed temperature is a time differential of the programmed temperature of the heating furnace at the time of measuring the temperature deviation.

2. A thermal analyzer according to claim 1, further comprising:

a temperature deviation approximation formula retrieval unit which is connected to the programmed temperature generator, to the temperature deviation approximation formula holder and to the programmed temperature corrector, wherein the temperature deviation approximation formula retrieval unit:

receives an input of the programmed temperature from the programmed temperature generator;

retrieves the first rate of elevating or lowering temperature of the heating furnace, which is held in the temperature deviation approximation formula holder, by using, as a key, the second rate of elevating or lowering temperature of the programmed temperature of the heating furnace, the first rate of elevating or lowering temperature being in agreement with the second rate of elevating or lowering temperature of the programmed temperature; and obtains from the temperature deviation approximation formula holder and outputs to the programmed temperature corrector, the temperature deviation approximation formula which is included in the set with the retrieved first rate of elevating or lowering temperature at the time of measuring the temperature deviation;

wherein the programmed temperature corrector uses the temperature deviation approximation formula outputted from the temperature deviation approximation formula retrieval unit to correct the programmed temperature.

* * * * *